United States Patent [19]

Field et al.

[11] Patent Number: 4,926,859

[45] Date of Patent: May 22, 1990

[54] A MEDICAL TREATMENT DEVICE FOR TREATING AN UNDESIRED FORMATION IN A LIVING BODY

[76] Inventors: John E. Field, 1 Babraham Road, Cambridge, Great Britain, CB2 2RB; John P. Dear, Rapley, Oakley Road, Bromley, Great Britain, BR2 8HQ; Peter N. Davies, 2 Ditton Forest Cottages, Newmarket, Great Britain

[21] Appl. No.: 203,452
[22] PCT Filed: Dec. 4, 1986
[86] PCT No.: PCT/GB86/00737
   § 371 Date: Jul. 5, 1988
   § 102(e) Date: Jul. 5, 1988
[87] PCT Pub. No.: WO87/03468
   PCT Pub. Date: Jun. 18, 1987

[30] Foreign Application Priority Data

Dec. 4, 1985 [GB] United Kingdom ............ 8529824

[51] Int. Cl.$^5$ .............................................. A61F 5/46
[52] U.S. Cl. .................................. 128/24 A; 604/131
[58] Field of Search .................. 604/22, 27, 30, 51, 604/70, 131; 128/328

[56] References Cited

U.S. PATENT DOCUMENTS 3,115,133 12/1963 Morando ............................ 604/70
3,788,315 1/1974 Laurens ......................... 128/173 H

FOREIGN PATENT DOCUMENTS 3421390 12/1985 Fed. Rep. of Germany ...... 128/305

OTHER PUBLICATIONS

Dr. F. P. Bowden, C.B.E., F.R.S., and J. H. Brunton, "Damage to Solids by Liquid Impact at Supersonic Speeds", *Nature,* vol. 181, pp. 873–875, Mar. 29, 1958.
Powell, P. C., "Engineering with Polymers", Champman & Hall, p. 35, 1983, (ISBN0412241709).

*Primary Examiner*—Jerome L. Kruter
*Attorney, Agent, or Firm*—Merchant, Gould, Smith, Edell, Welter & Schmidt

[57] ABSTRACT

Medical treatment device for treating a target in a living body which takes the form of an undesired solid formation, such as a kidney stone (13). The device comprises a chamber (7) for accommodating a charge (5) of low density material, such as a liquid, semi-liquid material or a gel, a nozzle (11) forming an outlet from the chamber, and a receiving aperture closed by a diaphragm (9) which communicates with the chamber (7) and which is arranged to receive a slug (3) of relatively high density material projected at high speed towards the aperture, thereby to transmit the impacting force of the slug to the charge in the chamber so that the charge is extruded through the nozzle (11) as a pulsed jet. The slug is propelled at high speed along a barrel (25, 41) upon supply of high pressure gas under the control of a quick-acting valve (27), and a guide tube (31) is connected to the nozzle (11) and is arranged to direct the pulsed jet which issues from the nozzle, substantially without loss of kinetic energy, and towards the target so as to effect cleavage of the solid formation.

10 Claims, 3 Drawing Sheets

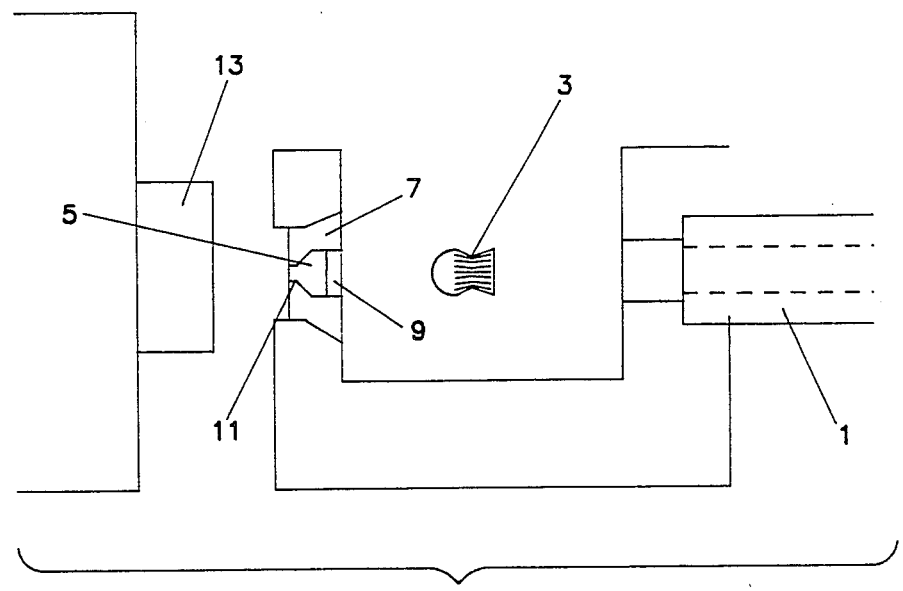
FIG. 1
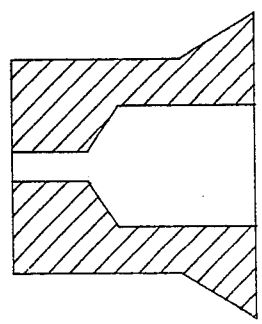  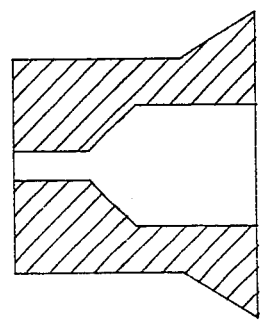  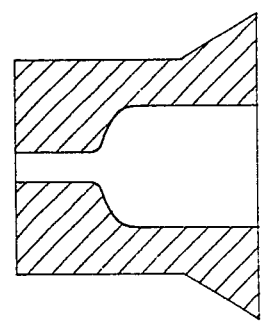
FIG. 2A    FIG. 2B    FIG. 2C

A MEDICAL TREATMENT DEVICE FOR TREATING AN UNDESIRED FORMATION IN A LIVING BODY

BACKGROUND OF THE INVENTION

This invention relates to a medical treatment device for treating an undesired solid formation in a living body, by bombardment of the formation with a pulsed liquid or semi-liquid jet.

The invention has been developed primarily with a view to treating undesired solid formations in human patients, examples of such undesired formations including stones (especially kidney stones), though other growths and deposits in the human body may be treated, including natural or artificial deposits, such as cements used in bone joint replacements.

The term "treating" used herein is intended to include fragmentation, total removal or cleaning.

A medical treatment device according to the invention is particularly suitable for use in the removal of kidney stones, by progressive bombardment of the stones so as to cause fragmentation of the stones into small fragments which can then be removed by a surgeon by any convenient means, such as an endoscope.

Kidney stones generally form because of a metabolic abnormality which increases the concentration of crystaloids in the urine. The stones consist mainly of inorganic salts of calcium although salts of uric acid, oxalic acid and phosphoric acid may also occur depending on the long term acidity or alkalinity of the urine. The stones may vary in size from grits up to golf ball dimensions and in consistency from soft or cheesy to hard and brittle. In the majority of cases, the stones are passed spontaneously along the urethra but many of the larger ones lodge in the kidney pelvis or calyses where they would, in general, require open surgery to remove them. Such surgery might involve extracting the stones through a small hole or, in severe cases, a partial or total nephrectomy, that is a removal of the kidney. Whichever method is used the recovery and convalescene period is that required for many other major operations.

A general surgical procedure which has been used for some years is minimal intrusion surgery or endoscopic surgery in which endoscopes having tubes of small dimensions are introduced into the body through what amounts to a small puncture hole in the muscles, skin and organ being operated on. It would be advantageous to be able to treat kidney stones using endoscopic techniques. An endoscope can be introduced into the vicinity of a kidney stone but such a stone may be too large to be extracted through the endoscopic tube. Such stones would have to be broken up into smaller pieces in order that they could be extracted.

The invention seeks to provide a medical treatment device which is able to be used, inter alia, in the removal of a kidney stone, in that it is concerned with the bombardment of the kidney stone with a pulsed high velocity charge of low density material which cleaves the stone into fragments which may be then removed.

The low density material of which the charge is composed may be water or other suitable liquid, or a liquid based material which is rendered semi-liquid or at least partly "solid" by introduction of an additive to the liquid. One preferred example of the latter comprises a "gel" which is obtained by adding controlled amounts of gelatine to water, typically in an amount of a few percent. A gel can be prepared for use in a device according to the invention, which takes any desired form within the range of a liquid through to a solid.

A kidney stone may be cleaved by a high velocity short duration charge because of the intense pressure created as a result of impact between the charge (when it includes a liquid component) and the stone. This is due to the compressible behavior of the charge in the initial stages of the impact. The pressure, for a rigid target, is given by the equation $P = pCV$ where p is the liquid density, C is the shock wave velocity in the liquid and V the impact velocity. The pressure is referred to as a "water-hammer" pressure and continues as long as the contact area between the impacting charge and the solid expands supersonically with respect to waves in the liquid. The duration of this stage depends on the impact velocity and the radius of curvature of the head of the charge but is generally in the range 0.1 to 1 microseconds.

The short duration of the liquid charge has the advantage that there is minimal movement of the impacted body compared with, for instance, impacting a kidney stone by means of a solid projectile.

The high velocity charge or "jet", after it emerges from the nozzle or orifice, remains coherent in air for typically a few centimeters, the precise distance depending on many factors, including the jet velocity, diameter, density and surface tension. The coherence distance is also dependent on the density of the fluid traversed by the jet. Within a more dense fluid such as a liquid the distance over which the jet remains coherent is reduced. This is an advantage in treating kidney stones because if the stone is missed by the jet, the damage capability of the jet at surfaces further away is considerably reduced.

SUMMARY OF THE INVENTION

According to one aspect of the invention there is provided a medical treatment device for treating a target in a living body which takes the form of an undesired solid formation, the device comprising:

a chamber for accommodating a charge of material having a relatively low density;

a nozzle forming an outlet from said chamber;

a receiving aperture communicating with the chamber and arranged to receive a slug of relatively high density material projected at high speeds towards the aperture, thereby to transmit the impacting force of the slug to the charge in the chamber so that the charge is extruded through the nozzle as a pulsed jet;

means for projecting the slug towards the receiving aperture; and a guide tube connected to the nozzle and arranged to direct the pulsed jet, issuing from the nozzle, substantially without loss of kinetic energy and toward the target so as to effect cleavage of the solid formation.

Thus, in use of the device, the guide tube may be taken into the interior of the body of a patient, after suitable surgery, so as to be located sufficiently close to the target e.g. a kidney stone, to ensure cleavage of the stone, but the remainder of the device will be located externally of the body of the patient.

The material of which the charge is composed may comprise a droplet of water, or may be a water based composition including, if desired, antiseptic material. When the charge is water, or other liquid, it is preferred to arrange a closure member to extend across the receiving aperture, which holds the liquid charge in position until the slug makes impact with the closure member and the latter is then displaced so as to transfer the impact of the slug to the liquid charge. The closure member may comprise a diaphragm or elastomeric disc.

A preferred alternative material for the charge comprises a liquid-based material which does not require retention in position by a closure member, but which is sufficiently "solid" to retain itself in position in the chamber. A "gel" is particularly suitable.

The means for projecting the slug towards the receiving aperture takes any suitable form, somewhat similar to an "air gun". Thus, the means may comprise a barrel, a breech into which the slug can be loaded, a reservoir for storing a compressed gas, and a quick-acting valve which can be operated to effect rapid release of the gas pressure in the reservoir to act on the slug.

To render the device particularly suitable for hand-held use by a surgeon, it is preferred that the barrel is arranged to extend at least partly into a pressure cylinder forming the reservoir, whereby the overall length of the device can be reduced to a convenient hand-held size.

The valve for controlling communication between the pressure cylinder and the barrel (when the barrel extends partly into the cylinder) may comprise a piston member movable within a housing between a first position closing one end of the barrel and a second position in which the barrel is brought into fluid communication with the pressure cylinder, the housing having an outlet closed to atmosphere but which is openable to permit rapid evacuation of pressurised fluid from the housing to cause the piston member to move from its first to its second position.

According to a further aspect of the invention there is provided a medical treatment device for treating a target in a living body which takes the form of an undesired solid formation, the device comprising:

a chamber for accommodating a charge of material having a relatively low density;

a nozzle forming an outlet from said chamber;

a receiving aperture communicating with the chamber and arranged to receive a slug of relatively high density material projected at high speed towards the aperture, thereby to transmit the impacting force of the slug to the charge in the chamber so that the charge is extruded through the nozzle as a pulsed jet;

a barrel for accommodating the slug, the barrel communicating at one end with said chamber; and a pressure cylinder for storing high pressure gas and connected to the barrel via a valve, the valve being operable to cause the cylinder to be brought into fluid communication with the barrel to apply fluid pressure to the slug so as to project the latter towards the charge, at least part of the length of the barrel extending within the pressure cylinder.

According to another aspect of the invention there is provided a medical treatment device for treating a target in a living body which takes the form of an undesired solid formation, the device comprising:

a chamber for accommodating a charge of material having a relatively low density;

a nozzle forming an outlet from said chamber;

means for projecting a slug of relatively high density material into the chamber to cause the charge to be extruded through the nozzle to emerge from the chamber as a pulsed jet;

a pressure cylinder for storing high pressure gas;

a barrel for accommodating the slug, the barrel communicating at one end with said chamber and being connected to the pressure cylinder via a valve, the valve being operable to cause the pressure cylinder to come into fluid communication with the barrel to apply fluid pressure to the slug so as to project the slug towards the charge; and a piston member forming said valve and movable within a housing between a first position closing one end of the barrel and a second position in which the barrel is in fluid communication with the pressure cylinder, the housing having a closed inlet which is openable to atmosphere to permit rapid evacuation of pressurised fluid from the housing to cause the piston member to move from its first position to its second position, and thereby to initiate firing of the slug towards the chamber under the action of the fluid pressure from the pressure cylinder to the barrel.

BRIEF DESCRIPTION OF THE DRAWINGS

The present invention will now be described, by way of example only, and with reference to the accompanying drawings, in which:

FIG. 1 illustrates the principle of producing a high velocity short duration jet;

FIG. 2 illustrates various nozzles which can be used to produce jets of different sizes;

Referring to FIG. 1 of the accompanying drawings, a gun 1 is arranged so as to be able to fire a high density metal slug 3 at a charge 5 of low density material located within chamber 7. The charge 5 may be a water drop, though other low density liquid or semi-liquid material may be used, or a "gel". When the charge 5 is a liquid it is sealed in chamber 7 by means of a neoprene disc or diaphragm 9. Opposite diaphragm 9 the chamber is provided with an orifice 11 through which the charge is extruded as a result of the slug impacting diaphragm 9 and moving it forward into the water drop. The resultant jet is caused to impact a target 13, which may comprise a kidney stone of a patient which requires treatment.

The nozzles illustrated in FIG. 2 allow jets of different diameters to be produced. A typical jet diameter size is from 0.4 to 2.4 mm. Nozzle A can product jets having a wide range of diameters from 0.4 to 3.2 mm. Nozzle B is particularly suitable for jets of about 0.4 mm and nozzle C is suitable for jets of about 0.8 mm.

The inner surfaces of the nozzles should be smooth and of the correct geometry. Typically the space defined within the nozzle includes a first portion having a diameter between 4 and 6 mm, preferably between 4.5 and 5 mm and more preferably about 4.8 mm. A second portion of the nozzle is a stepped portion which may be smoothly curved (nozzle C) or of conical shape (nozzles A and B). Typically the angle of the stepped portion (or the average angle where the stepped portion is curved) relative to the axis of the space defined by the nozzle is between 40° and 70° and preferred angles are about 45° or about 60°. A third portion of the spaces defined by the nozzle is the orifice portion which typically has a length of from 1 to 3 mm, preferably 1.5 to 2.5 mm and more preferably about 2 mm. The diameter of the orifice portion is from 0.4 to 3.2 mm, preferably 0.3 to 1 mm and more preferably from 0.4 to 0.8 mm.

DESCRIPTION OF THE PREFERRED EMBODIMENT

Figure 3:
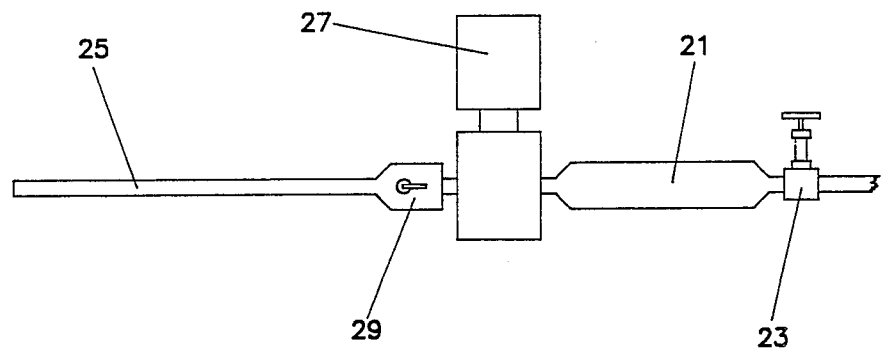
FIG. 3 illustrates schematically a part of a medical treatment device in accordance with the present invention.

Referring to FIG. 3, this illustrates a firing mechanism for projecting a slug of high density material at appropriate velocity towards a charge 5 of a liquid, a gel or other low density material. The mechanism includes a gas reservoir 21 which may be supplied with gas via gas supply valve 23. Pressurized gas loaded into reservoir 21 may be released into barrel 25 by means of fast acting solenoid valve arrangement 27. A slug loaded in the breech 29 is propelled down barrel 25 under the action of the pressurised gas. The arrangement may be calibrated so that a particular gas pressure produces a jet of the desired velocity.

Figure 4:
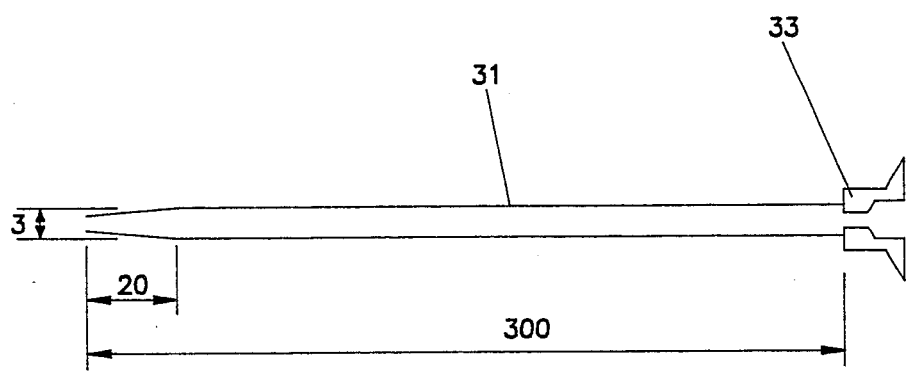
FIG. 4 shows a nozzle and focusing tube forming a further part of a device in accodance with the present invention.

Referring to FIG. 4, a focusing or guide tube 31 is connected to a device in accordance with the present invention so as to extend from the nozzle 33 of the device, and the arrangement is such that there is only minimal loss of kinetic energy of the high speed charge as it passes along the tube 31. This tube 31 serves to maintain the coherency of the jet and enables the jet to be produced outside the body with only the focusing tube itself extending into the body to the vicinity of the kidney stone. Typically the focusing tube may have a length of 300 mm. The end of the tube is tapered over a length of about 20 mm and the appropriate diameter of the tube is 3 mm.

A thin diaphragm made of, for example, plastics material, may be placed over the end of the tube 31 in order to prevent ingress of irrigant fluid into the tube. Such a diaphragm does not cause signifiant disruption of the jet. Using such a diaphragm, the jet can travel a distance of several mm from the end of the tube and still cleave a kidney stone. Alternatively the end of the tube may be sealed by a thin metal sheet. However, in this case the end of the tube may have to make contact with a kidney stone to ensure cleavage thereof and the mechanism of cleavage in this case is the production of a shock wave by the impact of the jet which passes through the metal and into the stone.

Figure 5A:
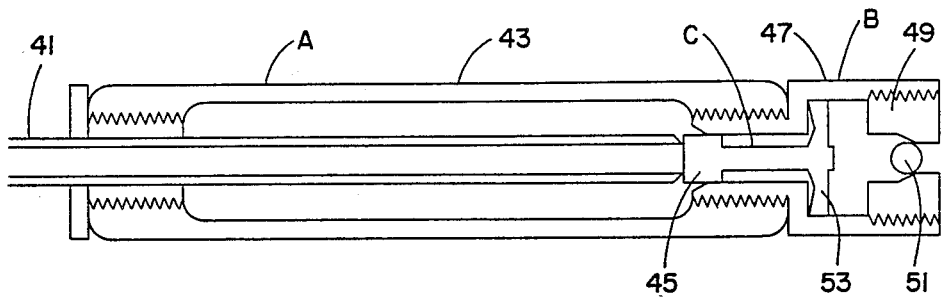
FIG. 5 shows a barrel, pressure cylinder and valve arrangement forming part of the device in accordance with the present invention.
Figure 5B:
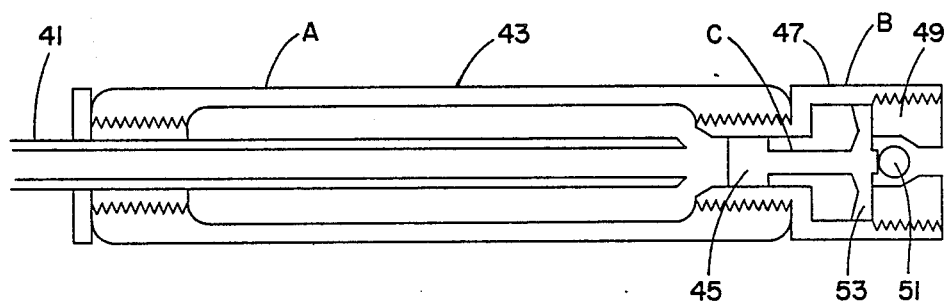

A device for use by a surgeon is desirably highly compact. The arrangement shown in FIG. 5 enables the overall length of the device to be considerably reduced. In this case, a barrel 41 extends through one end of pressure cylinder 43 and terminates within and close to the other end of the pressure cylinder. The barrel 41 is intended to fire a slug (not shown) at high speed in order to cause a jet of liquid or semi-liquid material to be propelled from a nozzle (not shown) and then along a focusing tube (also not shown) to the target. As a result of this "fold-back" arrangement of the barrel 41, the total length of the device is reduced by the length of the barrel lying within pressure cylinder 43.

In order to "fire" the gun it is necessary to rapidly apply the gas pressure from a cylinder 43 into the barrel 41. This is achieved by means of a trigger valve mechanism. One version of such a trigger valve includes parts B and C shown in exploded view in FIG. 5. The piston element C is accommodated within part B which is itself screwed into the end of pressure cylinder 43. Part B is in the form of a housing 47 having screwed into that end remote from pressure cylinder 43 a seat element 49 for a nylon ball 51. When the arrangement is ready for firing, piston 45 seals off the end of barrel 41 and there is a high pressure on both sides of its end disc portion 53. Firing is achieved by depressing the nylon ball 51 which causes gas within housing 47 to be rapidly vented from behind the piston 45. As a result the piston is thrust towards seat element 49 and high pressure gas enters the barrel 41, and drives the slug (not shown) after the latter has been loaded with the breech (also not shown) of barrel 41.

The arrangement of the device is such that the projectile can only be inserted after a nozzle has been loaded and pressurisation can only be performed after the projectile and nozzle are in position.

The material which forms the relatively low density drop may be a liquid such as water. The liquid may be encapsulated or in the form of a gel, either of which simplifies the loading of the liquid into the nozzle. The use of a liquid gel can improve the jet coherence.

A gel may be used, having liquid, semi-liquid or "solid" properties, as determined by the amounts of gelatine added to water. The gel will be a liquid-based material which has certain "solid" properties in that it may not require retention in position by the diaphragm 9, but is liquid constituent is able to form a pulsed jet upon impact by the slug.

The pH (acidity or alkalinity) of the liquid environment around a kidney stone has been found to affect its strength and hardness, and control of the pH of the liquid surrounding the stone could be used beneficially to assist in its break-up by the treatment device described herein.

We claim:

1. A medical treatment device for treating a target in a living body which takes the form of an undesired solid formation, the device comprising:
   a chamber for accommodating a charge of material of low density;
   a nozzle forming an outlet from said chamber;
   a receiving aperture communicating with the chamber and arranged to receive a slug of a density higher than said low density material projected at high speed towards the aperture, thereby to transmit the impacting force of the slug to the charge in a chamber so that the charge is extruded through the nozzle as a pulsed jet;
   means for projecting the slug towards the receiving aperture; and
   a guide tube connected to the nozzle and arranged to direct the pulsed jet, issuing from the nozzle, substantially without loss of kinetic energy and towards the target so as to effect cleavage of the solid formation.

2. A device according to claim 1, in which a closure member extends across the receiving aperture, thereby to hold a liquid charge in position until a slug makes impact with the closure member and the latter is then displaced so as to transfer the impact of the slug to the liquid charge.

3. A device according to claim 2, in which the closure member comprises a diaphragm.

4. A device according to claim 1, in which the means for projecting the slug towards the receiving aperture comprises a barrel, a breech into which the slug can be loaded, a reservoir for storing a compressed fluid, and a quick-acting valve which can be operated to effect rapid release of the pressure in the reservoir to act on the slug.

5. A device according to claim 1, in which the barrel is arranged to extend at least partly into a pressure cylinder forming said reservoir, whereby the overall length of the device can be reduced to hand-held size.

6. A device according to claim 5, in which the valve for controlling communication between the pressure cylinder and the barrel comprises a piston member movable within a housing between a first position closing one end of the barrel and a second position in which the barrel is brought into fluid communication with the pressure cylinder, the housing having an outlet closed to atmosphere but which is openable to permit rapid evacuation of pressurised fluid from the housing to cause the piston member to move from its first position to its second position.

7. A medical treatment device for treating a target in a living body which takes the form of an undesired solid formation, the device comprising:
   a chamber for accommodating a charge of material having a relatively low density;
   a nozzle forming an outlet from said chamber;
   a receiving aperture communicating with the chamber and arranged to receive a slug of relatively high density material projected at high speed towards the aperture, thereby to transmit the impacting force of the slug to the charge in the chamber so that the charge is extruded through the nozzle as pulsed jet;
   a barrel for accommodating a slug, the barrel communicating at one end with said chamber; and
   a pressure cylinder for storing high pressure gas and connected to the barrel via a valve, the valve being operable to cause the cylinder to be brought into fluid communication with the barrel to apply fluid pressure to the slug so as to project the latter towards the charge, at least part of the length of the barrel extending within the pressure cylinder.

8. A medical treatment device for treating a target in a living body which takes the form of an udesired solid formation, the device comprising:
   a chamber for accommodating a charge of material of low density;
   a nozzle formin an outlet from said chamber;
   means for projecting a slug of a density higher than said low density material into the chamber to cause the charge to be extruded through the nozzle to emerge from the chamber as a pulsed jet;
   a pressure cylinder for storing high pressure gas;
   a barrel for accommodating a slug, the barrel communicating at one end with said chamber and being connected to the pressure cylinder via a valve, the valve being operable to cause the pressure cylinder to come into fluid communication with the barrel to apply fluid pressure to the slug so as to project the slug towards the charge; and
   a piston member forming said valve and movable within a housing between a first position closing one end of the barrel and a second position in which the barrel is in fluid communication with the pressure cylinder, the housing having a closed inlet which is openable to atmosphere to permit rapid evcuation of pressurised fluid from the housing to cause the piston member to move from its first position to its second position, and thereby to initiate firing of the slug towards a chamber under the action of the fluid pressure from the pressure cylinder to the barrel.

9. A device according to claim 1, in which the charge comprises water, a water based composition, or a gel.

10. A device according to claim 2, in which the closure member comprises an elastomeric disc.

* * * * *